(12) United States Patent
Barrus (10) Patent No.: US 8,287,576 B2
(45) Date of Patent: Oct. 16, 2012

(54) MONO-AXIAL, TAPER LOCK BONE SCREW

(75) Inventor: Michael Barrus, Ashburn, VA (US)

(73) Assignee: K2M, Inc., Leesburg, VA (US)

( * ) Notice: Subject to any disclaimer, the term of this patent is extended or adjusted under 35 U.S.C. 154(b) by 331 days.

(21) Appl. No.: 11/877,607

(22) Filed: Oct. 23, 2007

(65) Prior Publication Data

US 2009/0105716 A1    Apr. 23, 2009

(51) Int. Cl.
- A61B 17/04 (2006.01)
- A61B 17/84 (2006.01)
- A61F 2/08 (2006.01)

(52) U.S. Cl. .................. 606/300; 606/305; 606/308

(58) Field of Classification Search .......... 606/264–276, 606/300–321, 279
See application file for complete search history.

(56) References Cited

U.S. PATENT DOCUMENTS

| | | | |
|---|---|---|---|
| 4,950,269 A | 8/1990 | Gaines, Jr. et al. | |
| 5,683,392 A | 11/1997 | Richelsoph et al. | |
| 6,010,503 A | 1/2000 | Richelsoph et al. | |
| 6,413,258 B1 | 7/2002 | Bernhardt, Jr. et al. | |
| 6,755,829 B1 * | 6/2004 | Bono et al. | 606/308 |
| 7,087,057 B2 * | 8/2006 | Konieczynski et al. | 606/278 |
| 7,090,674 B2 | 8/2006 | Doubler et al. | |
| 7,105,029 B2 | 9/2006 | Doubler et al. | |
| 7,118,303 B2 | 10/2006 | Doubler et al. | |
| 7,334,961 B2 | 2/2008 | Doubler et al. | |
| 7,335,201 B2 | 2/2008 | Doubler et al. | |
| 7,445,627 B2 | 11/2008 | Hawkes et al. | |
| 7,658,582 B2 | 2/2010 | Doubler et al. | |
| 7,678,136 B2 | 3/2010 | Doubler et al. | |
| 2005/0053423 A1 | 3/2005 | Doubler et al. | |
| 2006/0276792 A1 | 12/2006 | Ensign et al. | |
| 2007/0167949 A1 * | 7/2007 | Altarac et al. | 606/61 |
| 2007/0286703 A1 | 12/2007 | Doubler et al. | |
| 2008/0243193 A1 | 10/2008 | Ensign et al. | |

FOREIGN PATENT DOCUMENTS

WO    WO 2008/137933    11/2008

* cited by examiner

*Primary Examiner* — Eduardo C Robert
*Assistant Examiner* — Christina Negrelli
(74) *Attorney, Agent, or Firm* — Carter, DeLuca, Farrell & Schmidt, LLP (57) ABSTRACT

Provided is a novel mono-axial taper lock screw for connecting a connecting rod to bone. The screw is capable of being secured to the underlying bone while the screw head adapted to securely hold a connecting rod is rotated about the longitudinal axis of the screw to facilitate a stable connection to the connecting rod. The screw head can be partially locked to hold the device in place while permitting manipulation of the spine. The screw head can then be fully locked securing the connecting rod into a selected position. The screw is configured for easy insertion and connection as well as easy removal and disconnection from the connecting rod. Also provided is a bone fragments. A method of fixing bones or bone fragments is also provided.

19 Claims, 5 Drawing Sheets

MONO-AXIAL, TAPER LOCK BONE SCREW

BACKGROUND OF THE INVENTION

1. Field of the Invention

The present invention relates to orthopedic surgery and in particular to devices and prosthesis for stabilizing and fixing the bones and joints of the body. Particularly, the present invention relates to a mono-axial, taper lock screw for securing a connecting rod to a vertebra, wherein the screw can be easily inserted into a vertebra and connected to a connecting rod that can be connected to other vertebrae not on the same plane and can provide a structural configuration that facilitates ease of insertion or removal of the screw as desired. More particularly, the present invention relates to a novel mono-axial, taper lock bone screw configured to provide a mono-axial rotational connection of the screw to a connecting rod so as to permit surgical manipulation of the spinal vertebrae alignment and connecting rod positioning and then being capable of securing the connecting rod firmly in the selected position relative to the screw and the underlying attached bone. Further, the present invention relates to a mono-axial, taper lock bone screw having a proximal flange that is easily accessible to facilitate the connection of a complementarily configured gripping tool for improved ease of locking and unlocking of the screw when desired.

2. Background of the Technology

It is a common surgical requirement to stabilize and fix bones and bone fragments in a particular spatial relationship to correct the location of skeletal components due to injury or disease. This can be accomplished by using a number of bone pins, anchors, or screws placed in bones across a discontinuity in the bone or bone fragments, such as a fracture, or adjacent vertebrae, or joint. They are connected by a rod to maintain a predetermined spatial location of the bones or bone fragments. In some cases the use of these devices may be permanently implanted in the subject. In other cases, the devices may be implanted only as a temporary means of stabilizing or fixing the bones or bone fragments, with subsequent removal when no longer needed. It is also common that device implants that were intended to be permanent may require subsequent procedures or revisions as the dynamics of the subject's condition warrant. For these reasons, it is desirable that an implanted device be provided, which can be easily locked and unlocked as desired by the surgeon.

Spinal fixation apparatuses are widely employed in surgical processes for correcting spinal injuries and diseases. These apparatuses commonly employ longitudinally linked rods secured to the bone, such as vertebrae, by spinal bone fixation fasteners such as pedicle screws, hooks and others.

Many conventional bone screws do not provide a connection to a connecting rod wherein the connecting rod can be easily connected to adjacent vertebrae, which are not aligned on the same plane. Further, conventional bone screws do not allow any flexibility for alignment of the connecting rod in cases where a degree of flexibility would be desirable, such as, for example in treatment of the spine for scoliosis. Some effort has been made to provide screws that can be implanted into bone on varying planes; however, even for devices that have attempted to address the issue of securing rods to differently aligned vertebrae, such screws are not easily locked and unlocked and do not provide a mono-axial degree of flexibility and spinal manipulation that would be desirable in the treatment of some spinal conditions, such as scoliosis.

To meet the problem of securely connecting adjacent vertebrae, not on a common plane and that permit a mono-axial degree of flexibility for the screw head, a requirement exists to provide a mono-axial, taper lock screw that can be easily inserted and easily removed from the vertebral bone as desired. It is also desirable that such a screw be configured so that it can be locked into position in relation to the bone and the connecting rod without the need to exert any additional torque to the device or force on the patient. Additionally, such a mono-axial screw that can be used without the need for an additional locking piece, such as a set screw or the need to thread a locking device into place is desired.

Conventional efforts to treat such conditions, as for example, scoliosis, include the use of rigid screw and connecting rod connections. Such conventional connections fail to provide any degree of flexibility during the surgical procedure during which the surgeon manipulates and positions the spinal vertebrae into a desired alignment prior to locking the connecting rods into a rigid connection to the bone screws. More recently, polyaxial bone screws have been introduced and have greatly increased the ease of introducing and locking a connecting rod when building a spinal construct. However, flexible connections, such as polyaxial bone screws, provide too great a range of motion in cases such as scoliosis, and therefore, it is important that the flexibility during the spinal column manipulation process be restricted to allow only mono-axial movement of the connecting rod relative to the bone screw. The surgeon's manipulation forces on the spinal column and the implanted system should be effective in properly positioning the spinal column. However, if a conventionally provided connecting rod and screw system fails to limit the movements of the screw head to a single plane the force of the surgeon's manipulations could instead result in the head of the screw pivoting or rotating to one side or the other relative to the longitudinal axis of the spinal screw. Similarly, in the case of a rigid bone screw, spinal manipulation is more easily accomplished but attachment of the connecting rod is more difficult. Only a mono-axial screw head that limits movement to a single plane can avoid the unwanted multi-axial movement of the screw head during manipulation of the spine while still providing ease of attachment of the connecting rod. Further, conventional screw heads fail to provide a screw head configuration that presents ease of locking and unlocking the rod to the screw.

Thus a need exists for a system of screws and connecting rods that, during the surgical manipulation of the spine, is capable of permitting flexibility of the connecting rod position relative to the inserted bone screw in one plane while restricting movement in all other planes, thus, allowing only selected movement of the screw head-connecting rod attachment prior to locking the system in place. A need also exists for such a mono-axial, taper lock screw that is capable of being locked easily when grasped by a complementary configured tool that can be used by an operator for locking and unlocking the rod and screw.

SUMMARY OF THE INVENTION

The mono-axial taper lock screw provides a novel bone screw having the flexibility along a single axis that is needed to better facilitate the attachment of connecting rods to bone screws in the treatment of certain spinal conditions that require manual realignment or positioning of the spinal column prior to locking the spinal column into a selected position. Exemplary of such spinal conditions is scoliosis.

This novel screw also provides a mechanism for connection of a connecting rod to a first vertebra wherein the head of the screw is easily connected to a rod that can also be connected to an adjacent vertebra not in the same plane as the first vertebra and, due to a novel configuration of the head, can also be easily grasped by an operator using a complementary grasping tool to remove the screw when desired.

Also provided is a novel mono-axial taper lock screw configured to be easily connected to the vertebra and then connected to a connecting rod without the additional application of torque.

Also provided is a novel mono-axial taper lock screw configured to have a slidable outer housing over an inner housing containing a generally cylindrical configured, mono-axial rotational screw head and a removable connecting rod, wherein the outer housing can be selectively positioned to fully lock the screw head and the connecting rod in position within the inner housing.

Also provided is a novel mono-axial taper lock screw configured to have a slidable outer housing over an inner housing containing a cylindrical configured, mono-axial rotational screw head and a removable connecting rod, wherein the outer housing can be selectively positioned to fully lock the screw head and the connecting rod in position within the inner housing or can be selectively positioned to lock only the screw head in position while permitting a sliding and rotating motion of the connecting rod about its long axis within the inner housing.

Also provided is a kit that can include at least one of the novel mono-axial taper lock screws, at least one rod device, and surgical instruments having a configuration complementary to the configuration of the head of the novel screw and configured to facilitate grasping of the screw head for locking and unlocking of the rod.

Also provided is a method of using the novel mono-axial taper screw wherein the surgical procedure employed, in comparison to conventional methods, is quickly accomplished for locking or unlocking of the device.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein.

DETAILED DESCRIPTION OF THE INVENTION

Detailed embodiments of the present invention are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Figure 1:
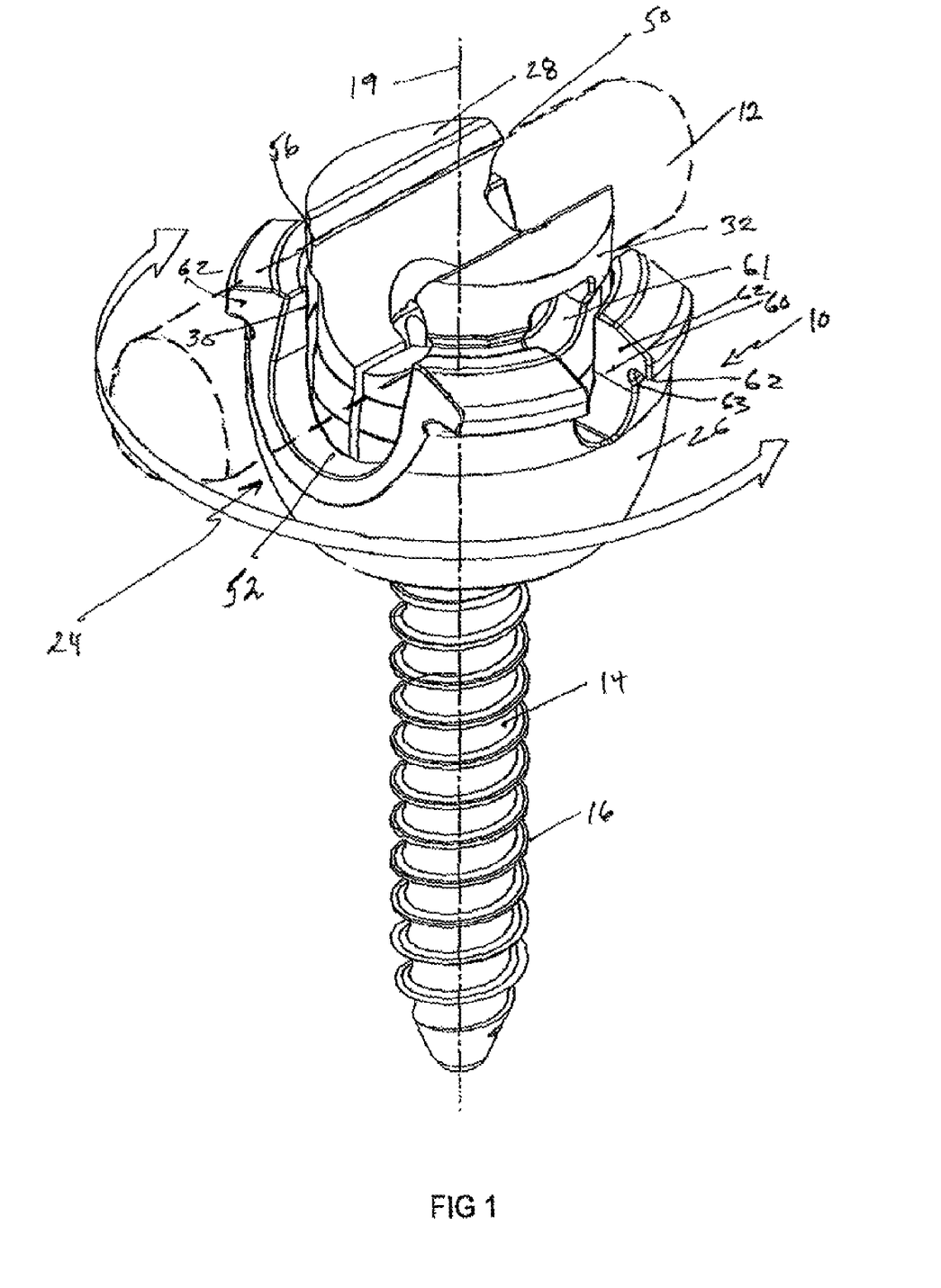
FIG. 1 shows an isometric view illustrating the mono-axial rotational capability of the novel mono-axial taper lock bone screw in an open position with a connecting rod (shown in dashed lines) positioned in the connecting rod slot of the screw.
Figure 2A:
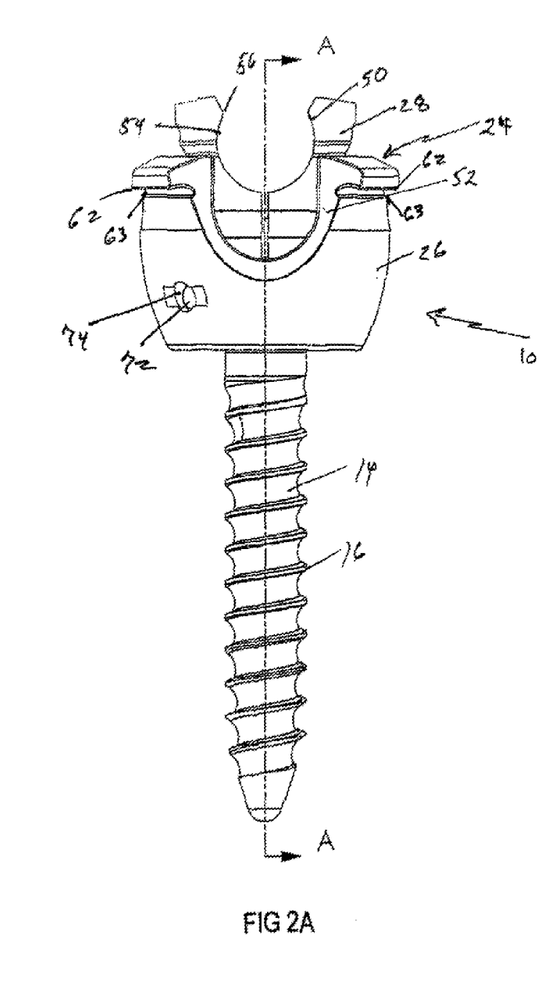
FIGS. 2A-B respectively show a side view of the novel mono-axial taper lock bone screw and a cross-sectional view of the same in an open position.
Figure 2B:
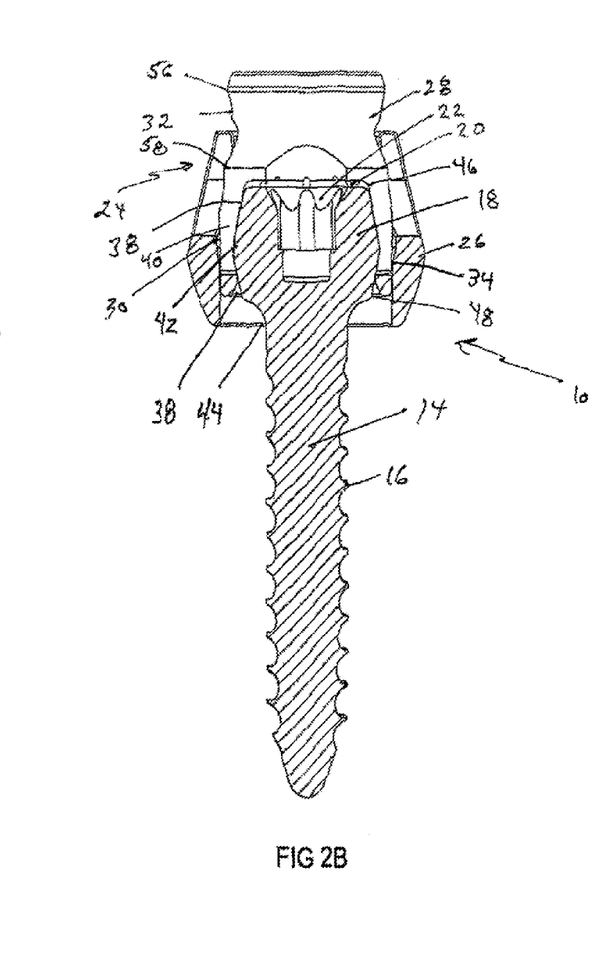

As shown in the accompanying figures a novel mono-axial tapered lock screw 10 is so configured so as to facilitate ease of insertion of the screw 10 into bone and connection to surgical devices, such as connecting rods, as well as facilitate easy locking and unlocking as desired FIG. 1 illustrates a connecting rod 12 (shown in dashed lines) positioned in the mono-axial screw 10. In the example shown, the connecting rod 12 is a rod having a generally circular cross section; however, it is within the concept of the invention to secure connecting rods of any suitable cross-sectional configuration required for the need at hand.

As shown in FIGS. 1, 2A-B, 3A-B, 4A-B, and 5A-B, the mono-axial taper lock bone screw 10 disclosed herein includes a screw shaft 14, which defines an external helical thread 16 for penetrating cancellous bone through the application of torque. The upper portion of the screw shaft 14 terminates in a screw head 18 that is symmetrically configured around the longitudinal axis 19 of the screw 10 and, in the exemplary embodiment shown in FIGS. 2B, 3B, 4A-B, and 5A-B, is generally proportioned to have a convex barrel-shaped outer surface. It is, however, with the inventor's conception that the screw head can have any symmetrical shape, other than spherical, so as to permit rotation of the screw head around the longitudinal axis 19 of the screw 10 without permitting polyaxial articulation within the inner housing 28. The upper surface 20 of the screw head 18 defines a screw head recess 22, which has a recess surface configuration that is complementary to the shape of a tightening and/or loosening tool. Without departing from the concept of the present invention, the screw head recess 22 can also be configured as a protrusion rather than a recess provided that the protrusion has a surface that is complementary for gripping attachment to a tool for tightening and/or loosening and provided that the height of the protrusion above the uppermost surface 20 of the screw head 18 is not such that it obstructs or interferes with any of the functions of the screw 10.

As best shown in FIG. 1, the screw 10 of the present invention is capable of connecting a connecting rod 12 by the use of a dual layered screw housing 24 that includes an outer housing 26 and an inner housing 28. The outer housing 26 is configured such that at least a portion of the inner surface 30 of the outer housing 26 is capable of selectively sliding over a portion of the outer surface 32 of the inner housing 28 in an upward and downward direction along the longitudinal axis of the screw 10. The configuration of both the outer housing 26 and the inner housing 28 are complementary in that when the outer housing is slid upward in relation to the inner housing at least one outer housing internal compression contact surface 34 is brought to bear against at least a portion of the outer wall 36 of the inner housing 28 and by that compressive force causes the inner housing 28 to in turn mechanically transmit that compressive force inward toward the central longitudinal axis of the screw 10.

A screw head articulation recess 38 is defined in the interior of the lower portion 40 of the inner housing 28. The interior surface 42 of the articulation recess 38 has a complementary surface configuration to the shape of the screw head 18. This complimentary configuration of the articulation recess facilitate mono-axial rotational articulation of the screw head 18 within the recess 38 around the longitudinal axis 19 of the screw 10 while prohibiting articulation of the screw head in any other plane relative to the longitudinal axis 19 and the screw shaft 14. The lower most portion of the inner housing 28 defines a screw shaft exit portal 44, that is sized small enough to retain the cylindrical screw head 18 within the recess 38. The recess 38 can include a recess upper edge 46 that is configured to selectively exert a locking compressive force against the screw head 18. A recess lower edge 48 can also be provided for the same purpose. Further, all or portions of the interior wall of the recess 38 can provide a compressive force against the screw head 18 that is sufficient to hold the screw head in a locked position.

The upper portion of the inner housing 28 defines an inner housing connecting rod slot 50 that is sized and configured to permit a connecting rod 12 to be placed transversely within the upper portion of the inner housing 28. An outer housing connecting rod slot 52 is also provided that is in common alignment with the inner housing connecting rod slot but is not necessarily of exactly the same measurement as the inner housing slot 50. The inner housing connecting rod slot 50 can define at least one compression contact surface 54 that when forced into compressive contact with a connecting rod 12 present in the slot 50, the contact surface can serve to securely hold the rod 12 in its relative position to the inner housing 28. Preferably the inner housing connecting rod slot 50 is provided with an opposing upper compression contact surface 56 and an opposing lower compression contact surface 58, which together can selectively be forced against the connecting rod 12 so as to secure and releasably lock it in place within the inner housing 28.

Preliminary to operation of the screw 10, the outer housing 26 should be positioned in the open position; that is it should be slid downward relative to the inner housing 28. The screw shaft 14 can then be driven into the cancellous bone by providing torsional force via a tool configured to mate with and grip the screw head recess 22. After the screw shaft 14 is positioned within the bone and the driving tool removed from the screw 10, a connecting rod 12 can be positioned transversely along the common course of and within the inner housing connecting rod slot 50 and the outer housing connecting rod slot 52.

In the treatment of certain spinal conditions, such as, for example scoliosis, the misaligned spinal column must be manually repositioned and realigned prior to locking the connecting rods into a rigid connection to the previously bone implanted spinal screws 10. As illustrated in FIG. 1, the novel mono-axial bone screw 10, in a partially locked or unlocked configuration allows mono-axial rotational movement of the outer housing 26 and inner housing 28 around the longitudinal axis 19 and the bone screw shaft 14. This articulation of the screw head facilitates positioning of the connecting rod to the screw and allows the surgeon to manipulate the spinal column as needed. Importantly, the flexibility of the connecting rod position relative to the inserted bone screw in one plane while restricting movement in all other planes allows only selected movement of the screw head-connecting rod attachment prior to locking the system in place. The surgeon's manipulation forces on the spinal column are more effective in properly positioning the spinal column because, while the mono-axial pivotal movement of the screw head-connecting rod attachment facilitates rod positioning and attachment, the complete restriction of movement of that attachment in any other plane serves to direct the applied manual force to its intended purpose, that of manipulating and realigning the spine. Failure to limit all other movement of the connecting rod-screw head attachment during the manipulation of the spine could instead result in the head of the screw pivoting or rotating over to one side or the other relative to the longitudinal axis of the spinal screw. Similarly, in the case of a rigid bone screw, spinal manipulations may be more easily accomplished but the connecting rod is unable to articulate in even a limited, mono-axial way thereby resisting the forces the surgeon needs to impose to realign the spine. Still further, attachment of the connecting rod to a rigid bone screw is more difficult due to the screws inability to modify its head position. The mono-axial screw head effectively restricts movement to a single plane, perpendicular to the longitudinal axis 19 of the screw 10, and thus avoids the undesirable multi-axial movement of the screw head during manipulation of the spine.

Figure 4A:
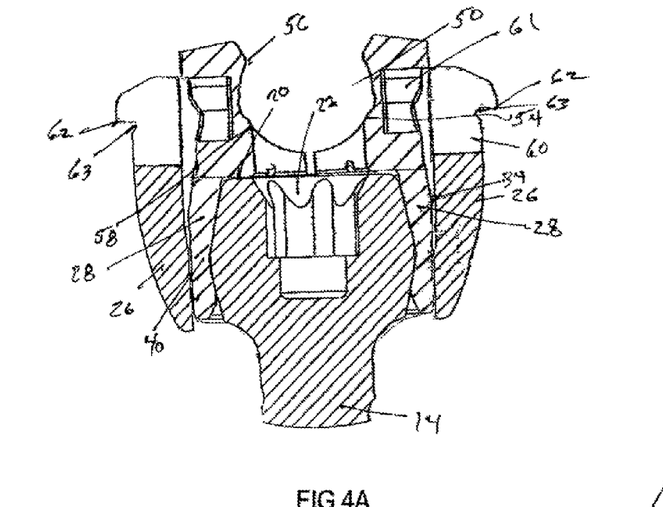
FIGS. 4A-B respectively show a cross-sectional view of the upper portion of the novel screw in an open position and a cross-sectional view of the upper portion of the novel screw securing a connecting rod in a closed position with directional arrows, which illustrate the inwardly directed compressive force of the outer housing against the inner housing.
Figure 4B:
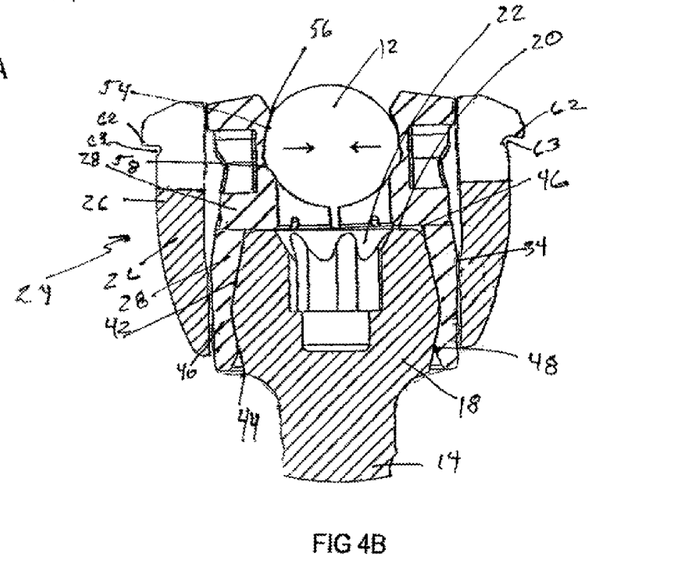

Following completion of all spinal manipulation and the resulting mono-axial movement of the connecting rod 12 and connecting rod slot 50, 52 relative to the bone embedded screw shaft 14, the construct can be locked into the selected position. To achieve locking of the mono-axial taper lock screw, the outer housing 26 can be grasped by the operator using a complementary configured grasping tool that when activated slides the outer housing 26 upward circumferentially over the outer surface of the inner housing 28 from the open or unlocked position to the closed or locked position, as shown in FIG. 4B. Similarly, the operator can use a complimentarily configured unlocking tool to grasp the inner housing 28 and slidably move the outer housing downward along the outer surface of the inner housing 28 from a closed or locked position to an open or unlocked position, as shown in FIGS. 1, 2A-B, 3B and 4A. The screw 10 can be provided with an inner housing access slot 60 defined through the wall of the outer housing 26, which provides access for the unlocking tool that is designed to make grasping contact with an inner housing tool receptor 61 to facilitate quickly unlocking the screw 10 and permitting movement of the screw head 18 within the articulation recess 38 and removal of the connecting rod 12 from the inner housing connecting rod slot 50.

Upward and downward sliding movement of the outer housing 26 relative to the inner housing 18 is facilitated by a housing guide pin 72, which is sized and configured for insertion through a guide pin hole 74 defined through the wall of the outer housing 26. The opening of the guide pin hole 74 is positioned over a guide pin slot 76 defined in the surface of the outer wall 36 of the inner housing 28. The guide pin slot 76 is sized and configured to slidably receive the inwardly directed proximal end 78 of the guide pin 72. The sliding movement of the proximal end 78 of the guide pin 72 within the guide pin slot 76 is limited side to side by the restrictions of the side walls 80 of the slot 76 and limited upward and downward by the upper end 82 and the lower end 84 of the slot 76.

The outer housing is provided with a receiving element 62 for the operator's tool, the receiving element 62 being formed by an outward extension of the upper portion of the outer surface of the outer housing 26. Preferably, the receiving element is a proximally located annular flange 62, which is formed as a generally radial extension from the upper third portion of the outside surface of the outer housing 26. More preferably, the annular flange 62 radially extends from a more elevated and therefore more operator accessible position from the upper quarter of the outer housing 26. Even more preferably, the annular flange 62 can extend from the upper fifth or less of the outer housing so long as the structural integrity of the flange connection to the outer housing during use is maintained. By way of example or relative proportions, if the outer housing has a height of approximately 0.400 inches, the lower lip of the flange would be approximately 0.076 inches from the top surface of the outer housing. This elevated position of the annular flange 62 provides a distinct advantage to the operator by positioning the annular flange 62 so as to not interfering with or obscure the surgeon's view of the anatomical structures at the surgical site or the surgeons access and ease of operation of the device during the insertion, locking and unlocking of the screw 10. As best shown in FIGS. 1, 2A, 3B, 4A-B, and 5A, the annular flange can be configured as a descending tapered lip around at least a part of the circumference of the upper portion of the outer housing. It is within the concept of the present invention that the annular flange 62 can have any functionally effective configuration provided it is proximally connected or integrally formed at the upper portion of the outer housing 26 and preferably formed within the upper third of the vertical length of the outer housing. The receiving element 26 can include an annular gripping groove 63, which is preferably located directly beneath the annular flange 62, which is best shown in FIGS. 1, 2A, 3B, 4A-B, and 5A. Similar to the annular flange 62, the annular gripping groove is present along at least a portion of the outer surface of the outer housing 26.

Figure 3A:
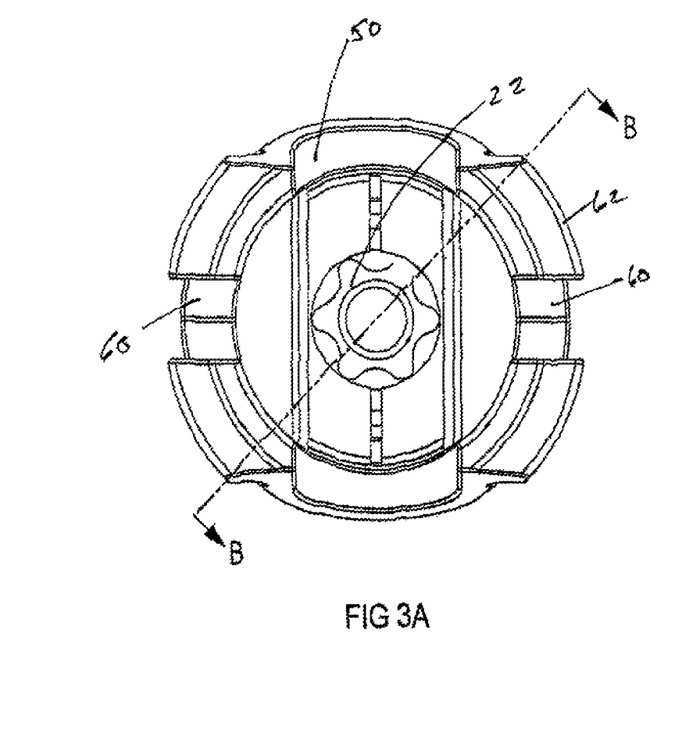
FIGS. 3A-B respectively show a top view of the upper portion of the novel mono-axial taper lock bone screw and a cross sectional view of the same in an open position.
Figure 3B:
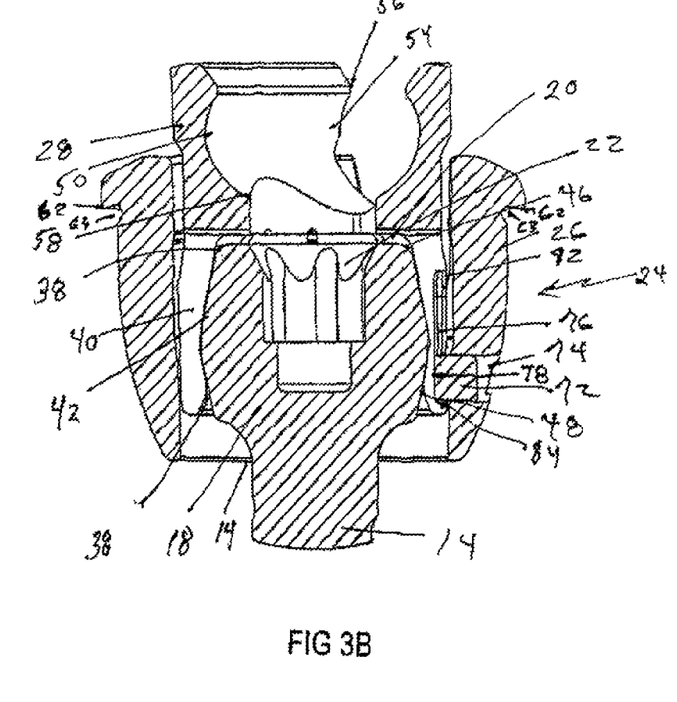

It is within the concept of the invention to selectively position the outer housing 26 along the surface of the inner housing 28 such that the compressive force exerted by the outer housing 26 on the inner housing 28 is such that a partial lock position can be attained; that is, by a limited sliding movement of the outer housing 26, compressive pressure will be exerted only on the articulation recess and the screw head 18 contained therein while the connecting rod 12 will remain free to slide transversely within the inner housing connecting rod slot 50. Using this partial lock of the screw 10, the operator can first position the screw 10 relative to the bone into which the screw shaft 14 has been attached and then manipulate the connecting rod 12 within the screw 10 to optimize its position before sliding the outer housing 26 into a full locked position on the inner housing 28. As best shown in FIGS. 3A and 4A, when the outer housing 26 is slid upward along the outer surface 32 of the inner housing 28 such that the screw 10 is in a fully locked or closed position, the uppermost extent of the outer housing 26 and the annular flange 62 are in a general alignment with the uppermost extent of the inner housing 28. In addition, with screw 10 in the fully locked position, the top of the connecting rod 12 is generally aligned with the uppermost extent of outer housing 26, the uppermost extent of inner housing 28 and the proximal flange. As can be seen in FIG. 4B, this provides a screw in a locked position in which there is substantially no profile above the connecting rod 12. This feature advantageously reduces the structure of the screw above the rod which might otherwise contact adjacent anatomical structures and cause pain or discomfort. The degree of this general alignment of the uppermost parts of the outer housing 26 and the inner housing 28 when the screw 10 is fully locked is demonstrated by comparison to the position of the uppermost parts of the outer housing 26 and inner housing 28 in the unlocked position, which is best shown in FIGS. 4A and 4B respectively.

Figure 5A:
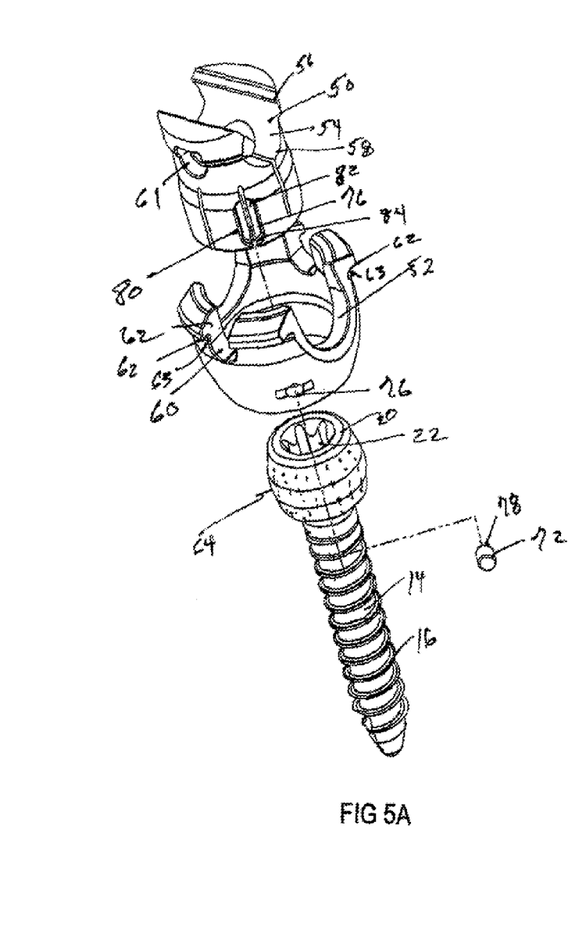
FIGS. 5A-B respectively show an exploded isometric view and an exploded side view of the novel mono-axial taper lock bone screw.
Figure 5B:
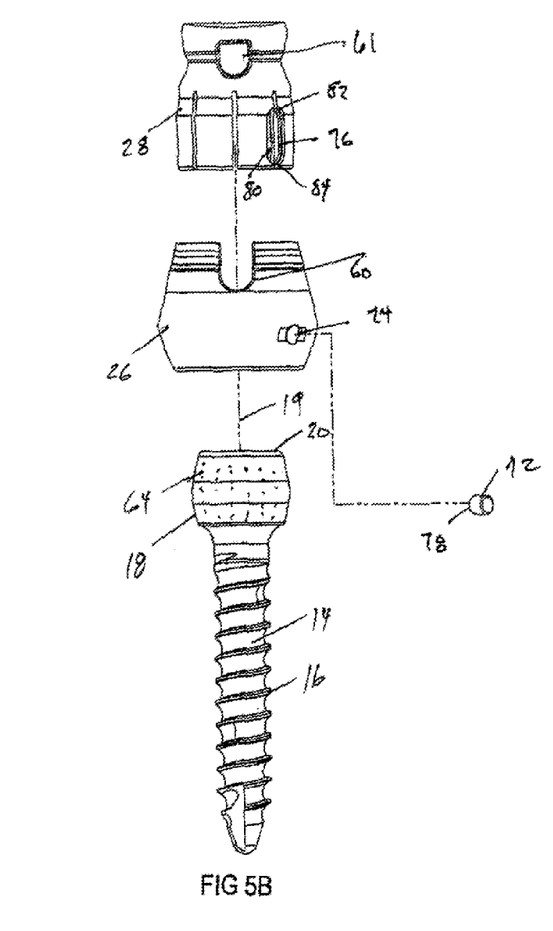

As shown in FIGS. 5A-B, unlike conventional bone screws, the mono-axial screw 10, when inserted into the bone and attached to a connecting rod 12 can provide a range of motion along a single plane, which is perpendicular to the longitudinal axis 19 and the screw shaft 14 of the screw 10. This flexibility is possible because of the symmetrical and complimentary shape of the screw head 18 and the screw head articulation recess 38, which allows movement of the screw head 18 within the inner housing 28. This movement is limited to a single or mono-axial direction by the restrictive complimentary shapes of the screw head 18 and the articulating recess.

This novel capability of the mono-axial screw to permit such a single plane rotational motion can be adapted to any bone screw that is configured to be capable of articulation of the portion of the screw to which the connecting rod attaches and the portion of the screw which is firmly secured to the underlying bone. While the concept is particularly well suited to the exemplary taper lock bone screw described herein, it is within the inventor's conception that the mono-axial rotational feature can be adapted to any articulating bone screw head wherein the locking function that is employed with other such screw heads is by a means other than a taper locking mechanism. Conventional locking mechanisms as are known in the art could be employed for the screw head while still adapting the mono-axial articulation capability described herein. This flexibility of adjusting the position of the screw head in a mono-axial fashion can also be used in future adaptations of bone screw heads having non-taper-lock locking mechanisms.

Provision of a textured surface 64, if desired, on the screw head 18 and/or the articulation recess 38, can serve to provide a degree of limited resistance to the operation of the mono-axial articulation provided by novel screw 10. Any type or degree of texturing or grooving of the surface can be employed in the manufacture of the screw 10 so long as the mono-axial articulation of the screw is not prohibited by the texturing.

The materials used to construct the present invention are those which have sufficient strength, resiliency, and biocompatibility as is well known in the art for such devices. Methods of manufacture of such surgical implant devices are also well known in the art.

It is within the concept of the present invention to provide the mono-axial taper lock screw 10 as part of a kit for use in a surgical process, the kit comprising at least two of the screws 10 and at least some of the associated tools for using the screws to connect a surgical rod to adjacent bones or bone fragments. In addition, the kit can contain surgical rods, such as, for example, connecting rods. Additional devices such as cross-connectors or links can also be included in the kit.

Each of the embodiments described above are provided for illustrative purposes only and it is within the concept of the present invention to include modifications and varying configurations without departing from the scope of the invention that is limited only by the claims included herewith.

What is claimed is:

1. A screw assembly comprising:
an inner housing and an outwardly disposed, slidably engaged outer housing, each of said inner and outer housing having a coincidentally aligned connecting rod slot that is sized and configured to circumscribe and hold at least a portion of a connecting rod, wherein said outer housing is capable of a sliding upward movement over said inner housing, said upward movement exerting a compressing force on said internally disposed inner housing to affect a locking action of said connection rod slot, wherein the outer housing is movable relative to the inner housing such that the inner and outer housings define a plurality of positions including an unlocked position, a partially locked position, and a locked position;
a bone screw having a screw head and a screw shaft, said screw head engaged within a screw head recess defined in said inner housing, the screw head and screw head recess each sized and configured such that the screw head and screw head recess may rotate about a longitudinal axis defined by the screw shaft, but are restricted from polyaxial articulation; and a connecting rod disposable in the connecting rod slot, wherein when the inner and outer housings define the partially locked position, the bone screw is axially fixed and the connecting rod is repositionable in the connecting rod slot.

2. The screw assembly according to claim 1, wherein said screw further comprises:
a guide pin;
a guide slot, said guide slot being defined in the outer surface of the wall of the inner housing and being sized and configured to enable sliding movement of said guide pin within said guide slot; and
a guide pin hole, said guide pin hole being defined through the wall of said outer housing at a position to facilitate passage of said guide pin through said guide pin hole and into said guide pin slot of said inner housing.

3. The screw assembly according to claim 1, wherein said screw head further comprises an upwardly disposed screw head gripping surface configured to receive a torsional tightening or loosening tool.

4. The screw assembly according to claim 1, wherein at or near the upper portion of said outer housing, said outer housing further comprises a proximally located annular flange projecting outward from at least a portion of the circumference of said outer housing, said annular flange being positioned and configured to be easily accessed and grasped by a grasping tool for facilitating transfer of an upward force to facilitating sliding of said outer housing upward over said inner housing.

5. The screw assembly according to claim 1, wherein said inner housing and said outer housing are configured such that internal compressive forces of said outer housing against said inner housing increase as said outer housing is slid progressively upward over said inner housing.

6. The screw assembly according to claim 1, wherein when said inner and outer housings define the fully locked position, said connecting rod is fixed in said connecting rod slot.

7. The screw assembly according to claim 1, wherein said outer housing is configured so as to exert a compressive locking force against said inner housing when said outer housing is slid to its upper most position relative to said inner housing.

8. The screw assembly according to claim 4, wherein said annular flange is disposed on said outer housing so as to overhang a circumferentially defined annular gripping groove, said gripping groove being configured to facilitate grasping contact of said grasping tool for facilitating locking of said screw.

9. The screw assembly according to claim 1, wherein said outer housing also comprises opposing inner housing access slots that are defined through the opposing walls of said outer housing, said inner housing access slot being sized and configured to allow access for a complementarily configured unlocking tool, grasping elements of which are sized and configured to pass through said inner housing access slots and make grasping contact with a respective inner housing tool receptor that is accessible through said inner housing access slots, whereby said inner housing can be grasped by said tool and moved in relation to said outer housing from the locked position to the partially locked position or further moved to the fully unlocked position.

10. A method for fixing bone comprising:
providing at least two screws, each screw including:
an inner housing and an outwardly disposed, slidably engaged outer housing, each of said inner and outer housing having a coincidentally aligned connecting rod slot that is sized and configured to circumscribe and hold at least a portion of a connecting rod, wherein said outer housing is capable of a sliding upward movement over said inner housing, said upward movement exerting a compressing force on said internally disposed inner housing to affect a locking action of said connection rod slot, wherein the outer housing is movable relative to the inner housing such that the inner and outer housings define a plurality of positions including an unlocked position, a partially locked position, and a locked position;
a bone screw having a screw head and a screw shaft, said screw head engaged within a screw head recess defined in said inner housing, the screw head and screw head recess each sized and configured such that the screw head and screw head recess may rotate about a longitudinal axis defined by the screw shaft, but are restricted from polyaxial articulation;
providing at least one connecting rod;
connecting said at least two screws to adjacent bones or bone fragments;
connecting said at least one connecting rod to each of said screws;
positioning said at least one connecting rod in the selected position;
as necessary adjusting the position of said at least one connecting rod relative to said screw and fully locking said screws.

11. The method of claim 10, further comprising, prior to the connecting rod positioning step, the additional steps of:
maneuvering the alignment of the spinal vertebrae as necessary relative to each other to a desired position; and
rotationally adjusting the alignment of the connecting rod slot to facilitate ease of insertion and connection of a connecting rod therein.

12. The method of claim 11, further comprising the additional step of partially locking said screws.

13. A screw assembly comprising:
an inner housing having a recess and a pair of upstanding walls, the upstanding walls defining a first slot;
an outer housing having a central opening and a second slot, the inner housing being slidably disposed in the central opening of the outer housing such that the first slot and the second slot are aligned, the inner and outer housing repositionable relative to each other and defining a locked position, a partially locked position, and an unlocked position; and
a bone screw having a head and a shaft, the head disposed in the central opening of the outer housing, the shaft rotatable about a longitudinal axis thereof, the longitudinal axis of the shaft coaxial with a longitudinal axis of the outer housing.

14. The screw assembly of claim 13, wherein relative movement of the inner housing and the outer housing exerts a compressive force on the inner housing, the compressive force urging the upstanding walls of the inner housing towards each other.

15. The screw assembly of claim 14, further including a rod disposed in the first and second slots.

16. The screw assembly of claim 15, wherein when the inner and outer housings define a partially locked position, the rod is fixed relative to the inner and outer housings and the shaft is rotatable.

17. The screw assembly of claim 15, wherein when the inner and outer housings define a locked position, the rod is fixed relative to the inner and outer housings and the shaft is axially secured with respect to the inner and outer housings.

18. The screw assembly of claim 13, wherein the longitudinal axis of the shaft and longitudinal axis of the outer housing remain coaxial during rotation of the shaft.

19. The screw assembly of claim 13, wherein the longitudinal axis of the shaft and the longitudinal axis of the outer housing remain coaxial during movement of the shaft of the bone screw.

* * * * *